(12) United States Patent
Wilt

(10) Patent No.: US 10,884,010 B1
(45) Date of Patent: Jan. 5, 2021

(54) DIFFUSION CELL WITH RECIRCULATING RECEPTOR CHAMBER

(71) Applicant: PermeGear, Inc., Hellertown, PA (US)

(72) Inventor: Andrew Wilt, Kintnersville, PA (US)

( * ) Notice: Subject to any disclaimer, the term of this patent is extended or adjusted under 35 U.S.C. 154(b) by 0 days.

(21) Appl. No.: 16/881,179

(22) Filed: May 22, 2020

(51) Int. Cl.
| | |
|---|---|
| *G01N 35/10* | (2006.01) |
| *G01N 13/00* | (2006.01) |
| *G01N 15/08* | (2006.01) |
| *G01N 33/15* | (2006.01) |
| *G01N 35/00* | (2006.01) |

(52) U.S. Cl.
CPC ......... *G01N 35/1081* (2013.01); *G01N 13/00* (2013.01); *G01N 15/08* (2013.01); *G01N 33/15* (2013.01); *G01N 35/1004* (2013.01); *G01N 2013/003* (2013.01); *G01N 2013/006* (2013.01); *G01N 2035/00356* (2013.01); *G01N 2035/00534* (2013.01)

(58) Field of Classification Search
CPC ........... G01N 35/1081; G01N 35/1004; G01N 15/08; G01N 13/00; G01N 33/15; G01N 2013/006; G01N 2035/00534; G01N 2013/003; G01N 2035/00356
See application file for complete search history.

(56) References Cited

U.S. PATENT DOCUMENTS

| | | | |
|---|---|---|---|
| 4,594,884 A | 6/1986 | Bondi et al. | |
| 4,690,762 A | 9/1987 | Katsura | |
| 4,806,135 A | 2/1989 | Siposs | |
| 5,183,760 A | 2/1993 | Sweetana et al. | |
| 5,198,109 A | 3/1993 | Hanson et al. | |
| 6,497,157 B1 | 12/2002 | Viegas et al. | |
| 8,133,721 B2 | 3/2012 | Yang et al. | |
| 8,322,193 B2 | 12/2012 | Castro et al. | |
| 8,393,199 B2 | 3/2013 | Kamiyama et al. | |
| 2005/0019903 A1* | 1/2005 | Yang | G01N 13/00 435/288.2 |
| 2019/0353570 A1 | 11/2019 | Shaw et al. | |

* cited by examiner

*Primary Examiner* — Sally A Merkling
(74) *Attorney, Agent, or Firm* — Caesar Rivise, PC

(57) ABSTRACT

A diffusion cell includes: a donor chamber having bottom; a receptor chamber below and in fluid communication with the donor chamber, and having upper and lower ends; a membrane between and in contact with the bottom of the donor chamber and upper end of the receptor chamber, and adapted to diffuse some of the media in a liquid from the donor chamber to the receptor chamber; a conduit having a first port near the lower end of the receptor chamber and a second port above the first port and near the upper end of the receptor chamber; and a bubble trap in fluid communication with the upper end of the receptor chamber and having a third port higher than the second port; wherein circulation of a flow of fluid through the conduit and the receptor chamber removes bubbles from underneath the membrane and transports bubbles to the bubble trap.

22 Claims, 5 Drawing Sheets

DIFFUSION CELL WITH RECIRCULATING RECEPTOR CHAMBER

FIELD OF INVENTION

The present invention(s) relates to diffusion cells, including Franz Cells, as well as generally to methods for conducting transdermal diffusion cell testing and sampling useful in automated and manual diffusion sampling systems.

BRIEF DESCRIPTION OF THE DRAWINGS

Applicant's devices, systems, and methods will be described by way of example with reference to the accompanying drawings, in which.

BACKGROUND

A diffusion cell is used to research how long it takes for a substance to migrate into or through a membrane. A Franz Cell is a type of diffusion cell that Thomas Franz invented sometime in the 1970s. Franz Cells are used primarily in the development of compounds that are placed on the skin, but can also be used with other biological membranes like cornea, oral and nasal mucosa, stomach and intestinal linings, vaginal tissue, and nails. There are three main concerns when using a Franz Cell: bubbles, stirring, and sampling.

Figure 1B:
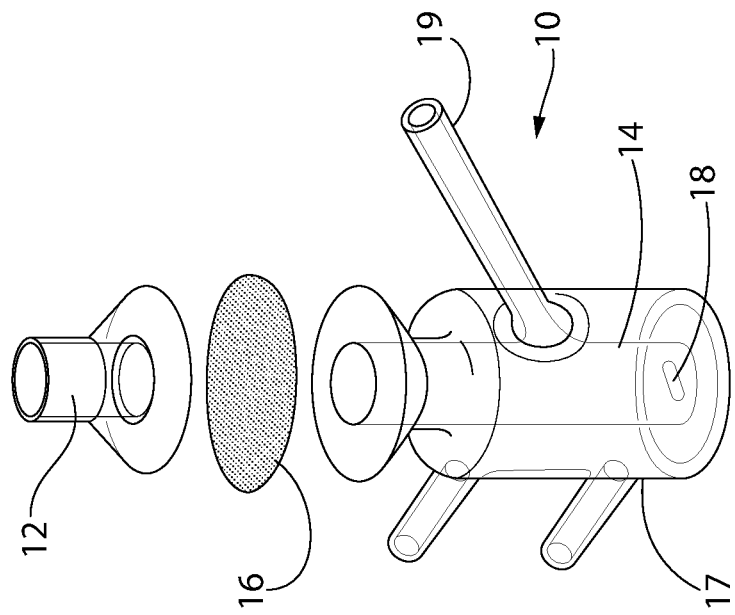
FIG. 1B is a perspective view of the diffusion cell of FIG. 1A including a heater jacket.
Figure 1A:
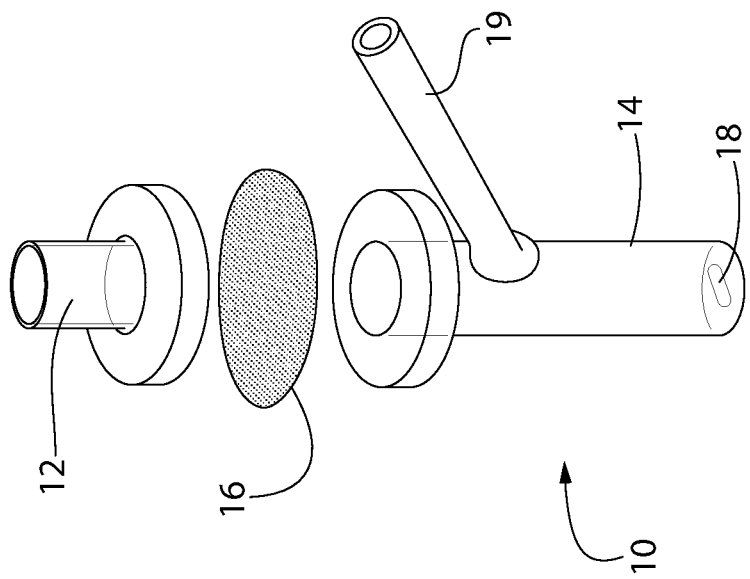
FIG. 1A is a perspective view of a diffusion cell in the prior art.

Two examples of Franz Cells are illustrated in FIG. 1A (without water jacket) and FIG. 1B (with water jacket). Franz Cells 10 include a donor chamber 12 and a receptor chamber 14. The two chambers are clamped together with a membrane 16 between the chambers using a cell clamp (not shown). The donor and receptor chambers are generally cylindrical in nature and the donor chamber 12 is located directly above the receptor chamber 14. The membrane 16 through which passage of the compound or media being studied is located in the horizontal plane between the chambers. Application of the compound or media of interest must cover the entire area of the membrane exposed to the donor chamber 12. Similarly, the liquid in the receptor chamber 14, which the compound or media may or may not enter, must be completely against the underside area of the membrane 16 that is exposed to the upper end of the receptor chamber 14.

In most any experiment, regardless of the liquids used in both chambers, bubbles will develop in the receptor chamber. Bubbles are problematic because they always rise to the top of the receptor chamber and dwell at the underside of the membrane. As the bubbles accumulate there, they often join together and eventually in the worst case scenario will completely prevent the liquid in the receptor chamber from being in contact with the membrane. This prevents the migration of the compound or media, if there is any, through the membrane and into the receptor fluid, and that makes for erroneous results.

If bubbles somehow enter the receptor chamber, they invariably congregate at the underside of the membrane because bubbles rise in liquid and the design of the Franz Cell receptor chamber is such that the underside of the membrane is the highest part of the receptor chamber. Bubbles gathering under the membrane often become enough in number that the underside of the membrane becomes physically separated from the receptor fluid and that negates the purpose of the experiment.

Franz Cells have the membrane in the horizontal plane and bubbles underneath the membrane must be dealt with. Bubbles will almost always form in a Franz Cell regardless of what steps have been taken to prevent them.

Because bubbles are formed in Franz Cell receptor chambers in the course of their use, the bubbles simply cannot be eliminated ahead of time and they must be dealt with in an ongoing manner. In manual systems where the Franz Cells are located in a multi-station magnetic stirrer, and sampled over short time intervals by technicians, Franz Cells can be removed from the magnetic stirrer and manipulated to remove the bubbles that have accumulated under the membrane. In automated systems that run unattended overnight, this is not possible. Removing the bubbles in manual systems means that the researchers cannot do other work and they are always concerned about the buildup of bubbles.

The attempted prevention of bubbles in Franz Cells is primarily done by degassing the receptor fluid. However, degassing removes only about 10% of the gases that typically form in the solutions used in Franz Cell receptor chambers. Heating the receptor fluid also helps, such as with a heated water jacket 17 as shown in FIG. 1B. Sonicating the receptor fluid, exposing it to ultrasound, also helps with degassing and heats the receptor fluid at the same time. However, regardless of these methods, bubbles will almost always form in the receptor chambers of Franz Cells and the acquisition of valid data requires constant monitoring of the Franz Cells.

Another problem with Franz Cells is that the stirring of the receptor chamber is not very good with the standard configuration. A stir bar 18 is shown in FIGS. 1A and 1B. These are rotated at 600 rpms, although other speeds are sometimes used, and although the stir bars 18 will generally cause the receptor fluid to be homogeneous, there are concerns about the effectiveness of stir bars 18.

Improvements in stirring include various devices, like Hanson's conical spring, that attach to the stir bars and do help with stirring. But many Franz Cells are used with only the stir bars supplied with them, just as they have been for the last 40 or more years.

Researchers measure the concentration of the compound of interest in the receptor chamber at various time intervals after the compound of interest is placed into the donor chamber on top of the membrane between the chambers.

Franz Cells are used in "manual" systems where the researcher withdraws samples from the receptor chamber using a pipette tip at regular time intervals. "Automated" Franz Cell systems use robotics and control systems to withdraw samples from Franz Cells unattended by people and can run throughout the night. But bubbles can easily become a problem, if not prepared for properly, when these unattended runs are happening because bubbles can insidiously appear unexpectedly for unknown reasons at any time.

The Franz Cells 10 shown in FIGS. 1A and 1B are used manually without automation. That is, samples are drawn through the sampling arm 19 by the researcher and taken for analysis. But Franz Cells are also used in automated systems that have robotic features which collect samples from multiple Franz Cells unattended and save them in vials which can be taken for analysis later. For example, pharmaceutical companies use automation to run many Franz Cells simultaneously in studies that are usually 24 hours in length but can be weeks long depending on the compounds used and the goals of the studies.

Because Franz Cells have changed so little over the years, the ones used in automation are similar to those shown in FIGS. 1A and 1B. There are others that don't have the manual sampling arm 19 but have porting to the receptor chambers that is located differently. The automated systems that use these cells combine computing power, electronics, pneumatics and/or hydraulics, robotics, and other technologies. They are complicated and maintaining their proper operation can be troublesome.

Solutions have been needed for the bubble problem, inadequate stirring, and complicated sampling for a long time.

BRIEF SUMMARY

There are various aspects of Applicant's recirculating diffusion cells, systems, and methods, and many variations of each aspect.

One aspect is a first diffusion cell that includes a donor chamber for containing a liquid and a media in the liquid, the donor chamber having a top and a bottom opposite the top; a receptor chamber below the donor chamber and in fluid communication with the donor chamber, the receptor chamber having an upper end and a lower end opposite the upper end; a membrane between and in contact with the bottom of the donor chamber and the upper end of the receptor chamber, the membrane adapted to diffuse a portion of the media in the liquid from the donor chamber to the receptor chamber; a conduit having a first port near the lower end of the receptor chamber and a second port opposite and above the first port and near the upper end of the receptor chamber; and a bubble trap in fluid communication with the upper end of the receptor chamber and having a third port positioned higher than the second port of the conduit; wherein circulation of a flow of fluid through the conduit and the receptor chamber removes at least some bubbles from underneath the membrane in the receptor chamber and transports at least some of said bubbles from the receptor chamber to the bubble trap.

In a first variation of the first diffusion cell, the third port is opposite the first port and above the second port of the conduit.

In a second variation of the first diffusion cell, at least a portion of the conduit is outside the receptor chamber.

In a third variation of the first diffusion cell, the conduit is adapted to transmit at least a portion of the flow of fluid from the upper end of the receptor chamber near the membrane through the second port into the conduit and downward to the first port and into the lower end of the receptor chamber.

In a fourth variation of the first diffusion cell, the conduit is substantially vertical.

In a variation of the fourth variation of the first diffusion cell, the conduit has a sampling port permitting removal of at least some of any contents of the receptor chamber.

In a variant of the variation in the paragraph above, removal of at least some of any contents of the receptor chamber through the sampling port is performed manually with a pipette tip.

In another variant of the variation two paragraphs above, removal of at least some of any contents of the receptor chamber through the sampling port is performed automatically with an automated pipette tip.

A second diffusion cell is similar to the first diffusion cell or any of the variations discussed above, but includes: an auger disposed in the receptor chamber; and a stir bar disposed in the receptor chamber and adapted to drive the auger; wherein the auger driven by the stir bar causes at least a portion of the flow of fluid to recirculate through the conduit and the receptor chamber, whereby said at least a portion of the flow of fluid is transmitted from the receptor chamber through the conduit and back into the receptor chamber.

A third diffusion cell includes: a donor chamber for containing a liquid and a media in the liquid, the donor chamber having a top and a bottom opposite the top; a receptor chamber below the donor chamber and in fluid communication with the donor chamber, the receptor chamber having an upper end and a lower end opposite the upper end; a membrane between and in contact with the bottom of the donor chamber and the upper end of the receptor chamber, the membrane adapted to diffuse a portion of the media in the liquid from the donor chamber to the receptor chamber; a substantially vertical conduit having a first port near the lower end of the receptor chamber and a second port opposite and above the first port and near the upper end of the receptor chamber; a bubble trap in fluid communication with the upper end of the receptor chamber and having a third port positioned higher than the second port of the conduit; an auger disposed in the receptor chamber, the auger having an upper end and a lower end; and a magnetically driven stir bar disposed in the lower end of the auger and adapted to drive the auger; wherein at least a portion of the substantially vertical conduit is outside the receptor chamber and the substantially vertical conduit is adapted to transmit a flow of fluid from the upper end of the receptor chamber near the membrane through the second port into the substantially vertical conduit and downward to the first port and into the lower end of the receptor chamber; wherein the auger driven by the magnetically driven stir bar causes at least a portion of the flow of fluid to recirculate downward through the substantially vertical conduit into the lower end of the receptor chamber and upward through the receptor chamber to the upper end of the receptor chamber, whereby the at least a portion of the flow of fluid is transmitted from the upper end of the receptor chamber through the second port downward to the first port and back into the receptor chamber at the lower end; and wherein recirculation of the at least a portion of the flow of fluid through the substantially vertical conduit and the receptor chamber removes at least some bubbles from underneath the membrane in the receptor chamber and transports at least some of said bubbles from the receptor chamber through the substantially vertical conduit to the bubble trap.

In a first variation of the third diffusion cell, the substantially vertical conduit has a sampling port permitting removal of at least some of any contents of the receptor chamber.

In a variation of the first variation of the third diffusion cell, removal of at least some of any contents of the receptor chamber through the sampling port is performed with a pipette tip.

Another aspect is a first automated system of diffusion cells that includes: a plurality of diffusion cells, each diffusion cell comprising a donor chamber for containing a liquid and a media in the liquid, the donor chamber having a top and a bottom opposite the top; a receptor chamber below the donor chamber and in fluid communication with the donor chamber, the receptor chamber having an upper end and a lower end opposite the upper end; a membrane between and in contact with the bottom of the donor chamber and the upper end of the receptor chamber, the membrane adapted to diffuse a portion of the media in the liquid from the donor chamber to the receptor chamber; a substantially vertical conduit having a first port near the lower end of the receptor chamber and a second port opposite and above the first port and near the upper end of the receptor chamber; a bubble trap in fluid communication with the upper end of the receptor chamber and having a third port positioned higher than the second port of the conduit; an auger disposed in the receptor chamber; and a magnetically driven stir bar disposed in the receptor chamber and adapted to drive the auger; wherein the auger driven by the magnetically driven stir bar causes a flow of fluid to recirculate through the substantially vertical conduit and the receptor chamber, whereby at least a portion of the flow of fluid is transmitted from the receptor chamber through the substantially vertical conduit and back into the receptor chamber; and wherein recirculation of at the least a portion of the flow of fluid through the substantially vertical conduit and the receptor chamber removes at least some bubbles from underneath the membrane in the receptor chamber and transports at least some of said bubbles from the receptor chamber to the bubble trap.

In a first variation of the first automated system, at least a portion of the substantially vertical conduit is outside the receptor chamber and the substantially vertical conduit is adapted to transmit the at least a portion of the flow of fluid from the upper end of the receptor chamber near the membrane through the second port into the substantially vertical conduit and downward to the first port and into the lower end of the receptor chamber.

In a variation of the first variation of the first automated system, the substantially vertical conduit has a sampling port permitting removal of at least some of any contents of the receptor chamber.

In a variant of the variation in the paragraph above, removal of at least some of any contents of the receptor chamber through the sampling port is performed automatically with an automated pipette tip.

A second automated system is similar to the first automated system or any of the variations discussed above, but includes: a magnetic console adapted to magnetically drive the magnetically driven stir bar.

Another aspect is a method for removing bubbles from a diffusion cell that includes two steps. The first step is providing a diffusion cell that includes: a donor chamber for containing a liquid and a media in the liquid, the donor chamber having a top and a bottom opposite the top; a receptor chamber below the donor chamber and in fluid communication with the donor chamber, the receptor chamber having an upper end and a lower end opposite the upper end; a membrane between and in contact with the bottom of the donor chamber and the upper end of the receptor chamber, the membrane adapted to diffuse a portion of the media in the liquid from the donor chamber to the receptor chamber; a substantially vertical conduit having a first port near the lower end of the receptor chamber and a second port opposite and above the first port and near the upper end of the receptor chamber; a bubble trap in fluid communication with the upper end of the receptor chamber and having a third port positioned higher than the second port of the conduit; an auger disposed in the receptor chamber; and a magnetically driven stir bar disposed in the receptor chamber and adapted to drive the auger. The second step is driving the auger by the magnetically driven stir bar, thereby causing at least a portion of a flow of fluid to recirculate through the substantially vertical conduit and the receptor chamber, whereby said at least a portion of the flow of fluid is transmitted from the receptor chamber through the substantially vertical conduit and back into the receptor chamber; wherein recirculation of at the least a portion of the flow of fluid through the substantially vertical conduit and the receptor chamber removes at least some bubbles from underneath the membrane in the receptor chamber and transports at least some of said bubbles from the receptor chamber to the bubble trap.

In a first variation of the method, a magnetic console magnetically drives the magnetically driven stir bar.

In a second variation of the method, at least a portion of the substantially vertical conduit is outside the receptor chamber and the substantially vertical conduit is adapted to transmit the at least a portion of the flow of fluid from the upper end of the receptor chamber near the membrane through the second port into the substantially vertical conduit and downward to the first port and into the lower end of the receptor chamber.

In a variation of the second variation of the method, the substantially vertical conduit has a sampling port permitting removal of at least some of any contents of the receptor chamber.

In a variant of the variation in the paragraph above, removal of at least some of any contents of the receptor chamber through the sampling port is performed automatically with an automated pipette tip.

DETAILED DESCRIPTION

For the purpose of promoting an understanding of Applicant's devices, systems, and methods, references are made in the text to exemplary embodiments of diffusion cells, only some of which are described herein. It should be understood that no limitations on the scope of Applicant's devices, systems, and methods are intended by describing these exemplary embodiments. One of ordinary skill in the art will readily appreciate that alternate but functionally equivalent materials, components, and designs may be used. The inclusion of additional elements may be deemed readily apparent and obvious to one of ordinary skill in the art. Specific elements disclosed herein are not to be interpreted as limiting, but rather as a representative basis for teaching one of ordinary skill in the art to employ Applicant's devices, systems, and methods.

It should be understood that the drawings are not necessarily to scale; instead, emphasis has been placed upon illustrating the principles of Applicant's devices, systems, and methods. In addition, in the embodiments depicted herein, like reference numerals in the various drawings refer to identical or near identical structural elements.

Moreover, terms such as "substantially" or "approximately" as used herein may be applied to modify any quantitative representation that could permissibly vary without resulting in a change in the basic function to which it is related.

Applicant's recirculating diffusion cell doesn't seek to eliminate the formation of bubbles, but instead accepts that bubbles will form and moves the bubbles away from the membrane to another location. Applicant's recirculating diffusion cell also addresses the previously discussed issues or problems of Franz Cells.

Figure 2:
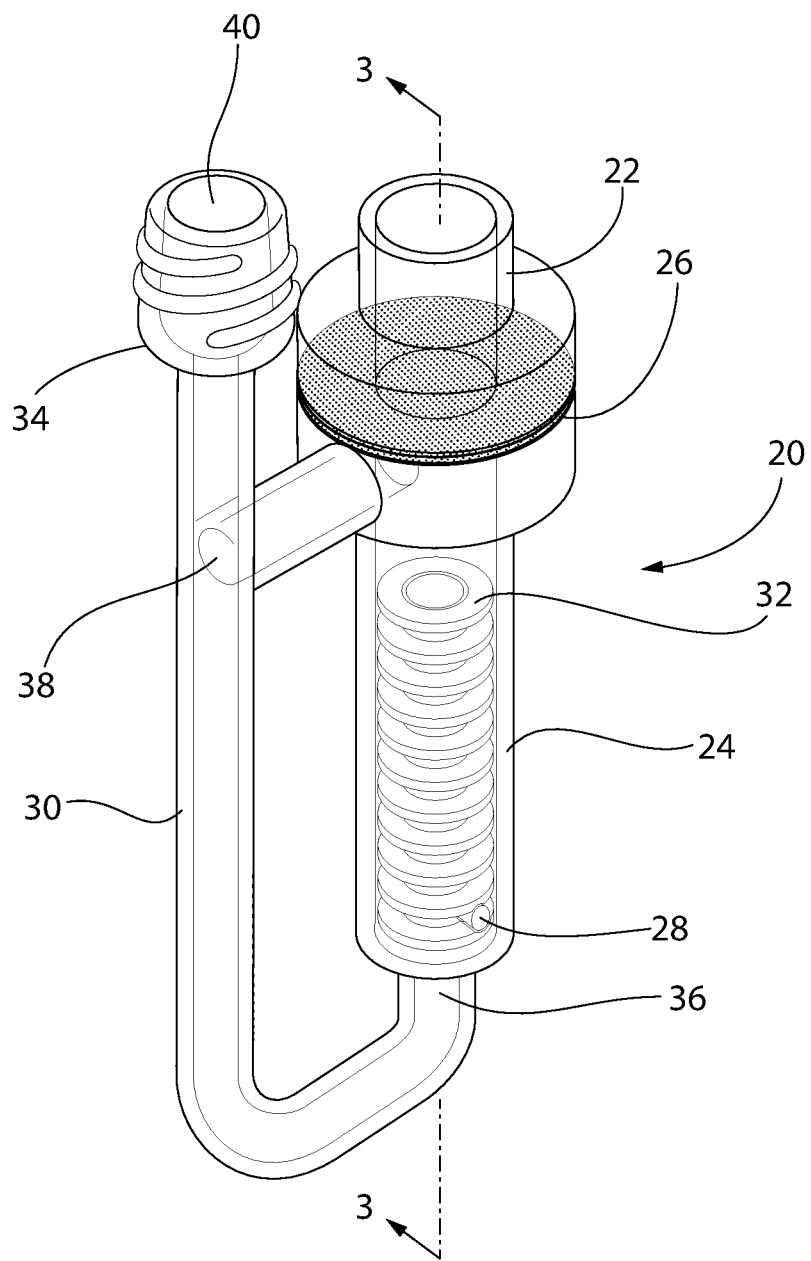
FIG. 2 is a perspective view of an exemplary embodiment of a diffusion cell.
Figure 3:
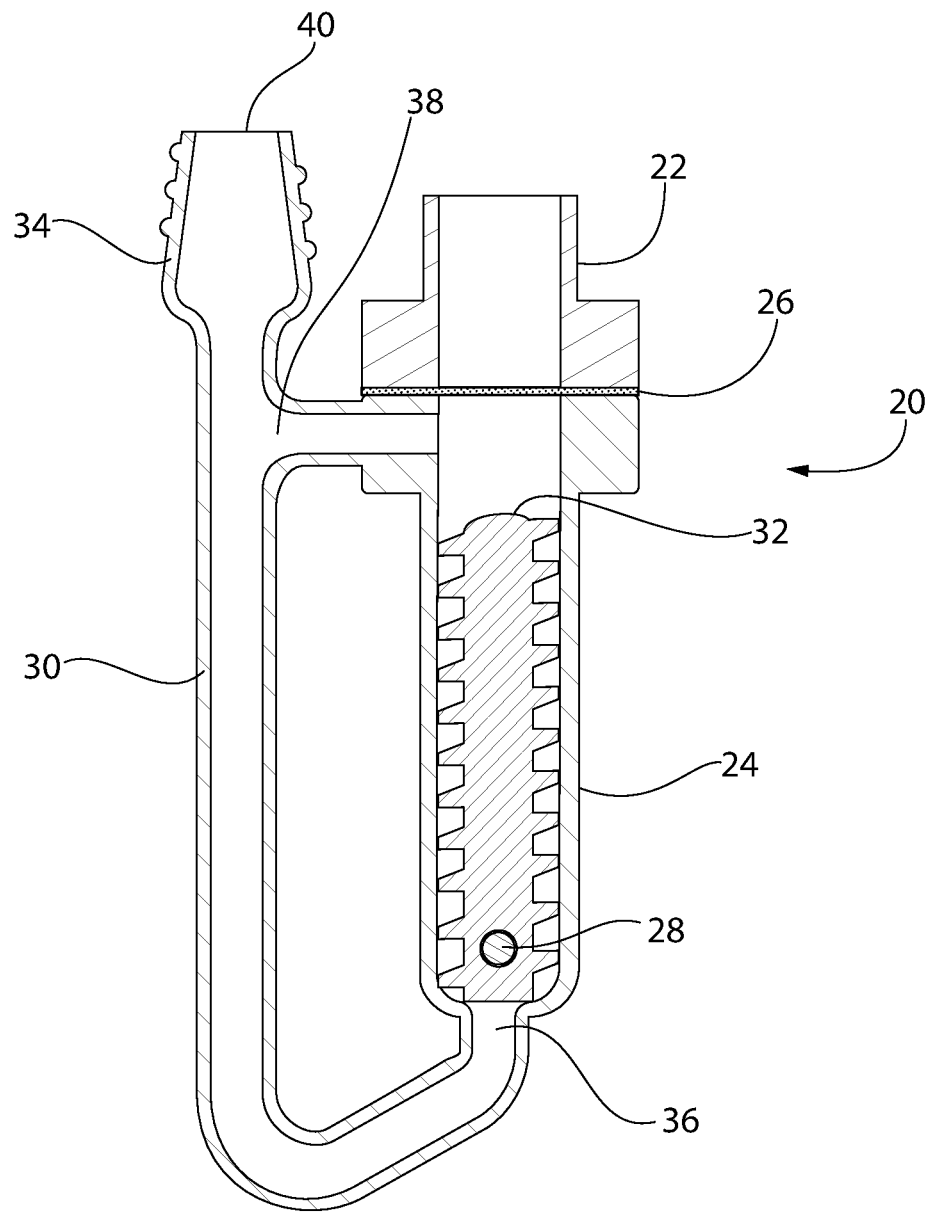
FIG. 3 is a sectional view of the exemplary embodiment of the diffusion cell shown in FIG. 2.
Figure 4:
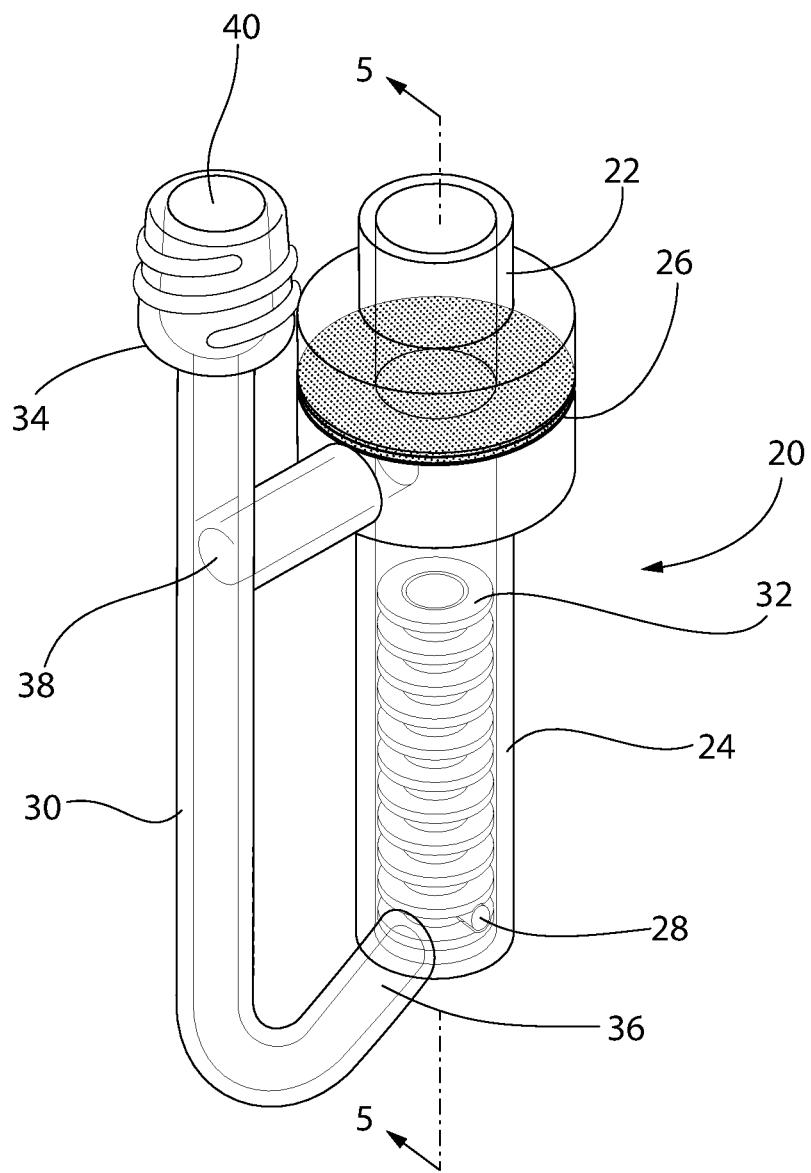
FIG. 4 is a perspective view of another exemplary embodiment of a diffusion cell.
Figure 5:
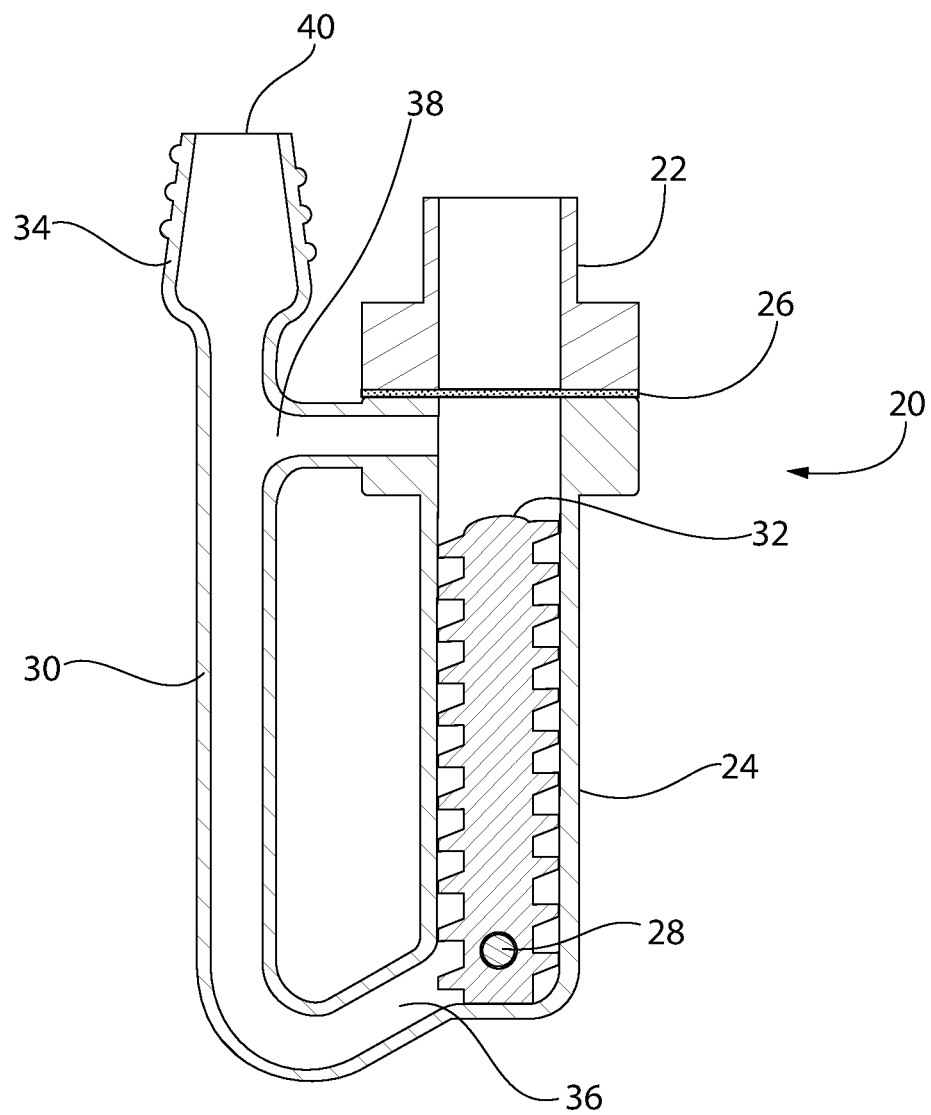
FIG. 5 is a sectional view of the exemplary embodiment of the diffusion cell shown in FIG. 4.

One embodiment of Applicant's recirculating diffusion cell 20 is illustrated in FIGS. 2 and 3. It has a donor chamber 22, receptor chamber 24, cell clamp (not shown), and stir bar 28, similar in some aspects to Franz Cells. However, the receptor chamber 24 has an external loop 30 or conduit which allows the flow of receptor fluid from the top of the receptor chamber 24 to a bubble trap 34 (an area where bubbles can be held) and down to the bottom of the receptor chamber 24. The external loop 30 or conduit may, for example, be a tubing made of glass or another appropriate material(s).

The external loop 30 or conduit of this embodiment includes three ports, as shown in FIGS. 2 and 3. The first port 36 at one end of the conduit is near the lower end of the receptor chamber 24, the second port 38 is near the upper end of the receptor chamber 24, and the third port 40 is at the opposite end of the conduit near the bubble trap 34. In this embodiment, fluid flows from the upper end of receptor chamber 24 near the membrane 26 through the second port 38 into the conduit or external loop 30 and downward to the first port 36 and into the lower end of the receptor chamber 24.

Applicant's recirculating diffusion cell also has an auger 32 or impeller which attaches to a magnetically driven stir bar 28 (magnet not shown) that causes the receptor fluid to move in the previously described fashion through the external loop 30. While the receptor fluid is recirculating around and around through the external loop 30 and the receptor chamber 24, the bubbles are forced away from the underside of the membrane 26 and captured in the bubble trap 34 in the upper area of the recirculating external loop 30.

Also, by virtue of the auger 32 or impeller action, the recirculating receptor fluid is vigorously mixed and the area directly under the membrane 26 is flushed well, thereby preventing a buildup of a concentration of the target compound or media which would impede further migration from the membrane 26 into the receptor chamber 24.

There is no "dead volume" of unstirred receptor fluid as in a conventional sampling arm. Substantially all of the fluid in the receptor chamber 24 is in motion during use of Applicant's recirculating diffusion cell 20.

Even if there are bubbles, the top of the auger 32 or impeller in this embodiment is located very near the underside of the membrane 26 so large bubbles simply can't form there. Smaller bubbles, such as those under approximately 2 mm in diameter, which might not be captured in the bubble trap 34, are continuously circulated so they don't adhere in one place to the underside of the membrane 26.

In the embodiments illustrated in FIGS. 2-5, the magnetically driven stir bar 28, which is inserted near the bottom of the auger 32, is a Teflon® coated permanent magnet. Stir bar 28 is driven by a rotating magnetic field generated by spinning a permanent magnet (not shown) below Applicant's recirculating diffusion cell 20 or by creating a rotating magnetic field electronically. In the case of the spinning permanent magnet alternative, the stir bar 28 is drawn toward the spinning permanent magnet as well as being spun by it. When the unit is turned off, the permanent magnet and the stir bar 28 will lock magnetically. In the other alternative, if a rotating magnetic field is created electronically with poles (not shown) beneath Applicant's recirculating diffusion cell 20, the stir bar 28 will be drawn toward those poles or will naturally stay in place by gravity when the unit is turned off.

If the electronically generated poles also are within vertical supports that hold Applicant's recirculating diffusion cell 20 in place during use, and are nearly as high as the membrane 26, the stir bar 28 possibly may not be drawn toward the bottom of Applicant's recirculating diffusion cell 20 when in use. Therefore, the threads of the auger 32 in the embodiments shown in FIGS. 2-5 are such that the fluid within the receptor chamber 24 is pushed up toward the membrane 26. The auger 32 therefore is pushed down at the same time and it is in contact with the bottom of the receptor chamber 24.

The upper portion of the recirculating external loop 30 is easily accessed vertically (e.g., with a pipette tip or other instrument) manually or by robotic means, no angular efforts are required, and so the ability to sample Applicant's recirculating diffusion cell 20 vertically addresses the problems of the complicated angular methods of many other devices and systems.

Applicant's recirculating diffusion cell 20 is a very good approach to addressing the bubble problem for various reasons, including but not limited to:

1—It allows a researcher to work with membranes in a horizontal plane.

2—The recirculation through the external loop or conduit and the receptor chamber is a more dynamic agitation method than conventional stirring and helps eliminate or minimize the boundary layer immediately below the membrane.

3—A conventional sampling arm, such as sampling arm 19 shown in FIGS. 1A and 1B, does not exist in Applicant's recirculating diffusion cell and therefore any dead volume, that is unstirred volume of receptor fluid within a sampling arm, is no longer an issue or concern.

4—Applicant's recirculating diffusion cells 20 while in use can be left in the vertical position, as opposed to tilting them in the Logan Instruments fashion, which means a researcher doesn't have to worry about what might happen in the donor chamber, specifically something draining or spilling out of it.

With regard to removal of all or substantially all of the receptor fluid from the receptor chamber, to Applicant's knowledge there is no known Franz Cell design that currently allows for that. Also, a substantial portion of the external loop 30 of Applicant's recirculating diffusion cell 20 is substantially vertical in the embodiments illustrated in FIGS. 2-5. That feature allows easy access by robotic mechanisms to withdraw the receptor fluid from the receptor chamber 24. Because part of the external loop 30 is the lowest part of the entire receptor volume, gravity will cause all or substantially all of the receptor fluid to go to that place where it can be withdrawn with an automated pipette tip.

The ability to remove all or substantially all of the receptor fluid is not the only advantage of the substantially vertical portion of the external loop 30. Elimination of an angular sampling arm (like sampling arm 19 in FIGS. 1A and 1B) allows the user to withdraw receptor fluid with an inexpensive pipette tip and not worry about unstirred contents of the receptor chamber 24. The receptor fluid recirculates substantially continuously through the receptor chamber 24 because of the pumping action of the auger 32, thereby eliminating or minimizing dead volumes or unstirred areas.

As discussed above with respect to the embodiments illustrated in FIGS. 2-5, some of the advantages of Applicant's recirculating diffusion cell 20 include, but are not limited to, the following:

1—Applicant's recirculating diffusion cell 20 removes bubbles from underneath the membrane 26 and traps them in the bubble trap 34, the upper accessible portion of the external loop 30.

2—The vertical orientation of a substantial portion of the external loop 30 of the receptor chamber 24 allows for easy sampling of small volumes or substantially all of the contents of the receptor chamber 24.

3—Refilling Applicant's recirculating diffusion cell 20 is easily done and it can remain in place because bubbles are moved by the action of the auger 32 and don't have to be removed manually by the user. This is particularly important because while an experiment is going on Applicant's recirculating diffusion cell 20 should remain in position in its magnetic stirrer console (not shown). With many prior art Franz Cells, to remove bubbles manually, one must turn the Franz Cell horizontally, if not somewhat upside down, and doing so can spill the contents of the donor chamber.

In addition to the exemplary embodiments illustrated in FIGS. 2-5, variations of those embodiments, as well as other embodiments, are possible. For example, external loop 30 may have other shapes, other types of augers or impellers may be used in place of auger 32, and stir bar 28 may have different shapes and/or be disposed at other locations in the receptor chamber 24.

Applicant's devices, systems, and methods include many other embodiments and variations thereof which are not illustrated in the drawings or discussed in the Detailed Description section. Those embodiments and variations, however, do fall within the scope of the appended claims and equivalents thereof.

Persons skilled in the art will recognize that the embodiments and variations illustrated in the drawings and discussed in the Detailed Description section do not disclose all of the possible arrangements of Applicant's devices and systems, and that other arrangements are possible. Accordingly, all such other arrangements are contemplated by Applicant's devices and systems, and are within the scope of the appended claims and equivalents thereof.

Persons skilled in the art also will recognize that many other embodiments incorporating Applicant's inventive concepts are possible, as well as many variations of the embodiments illustrated and described herein.

Although illustrated and described herein with reference to certain specific embodiments, Applicant's devices, systems, and methods are nevertheless not intended to be limited to the details shown. Rather, various modifications may be made in the details within the scope and range of equivalents of the claims without departing from the spirit of the invention.

What is claimed is:

1. A diffusion cell, comprising:
a donor chamber for containing a liquid and a media in the liquid, the donor chamber having a top and a bottom opposite the top;
a receptor chamber below the donor chamber and in fluid communication with the donor chamber, the receptor chamber having an upper end and a lower end opposite the upper end;
a membrane between and in contact with the bottom of the donor chamber and the upper end of the receptor chamber, the membrane adapted to diffuse a portion of the media in the liquid from the donor chamber to the receptor chamber;
a conduit having a first port near, and in fluid communication with, the lower end of the receptor chamber and a second port above the first port, the second port being near, and in fluid communication with, the upper end of the receptor chamber; and
a bubble trap in fluid communication with the upper end of the receptor chamber and having a third port positioned higher than the second port of the conduit,
wherein circulation of a flow of fluid through the conduit and the receptor chamber removes at least some bubbles from underneath the membrane in the receptor chamber and transports at least some of said bubbles from the receptor chamber to the bubble trap.

2. A diffusion cell as in claim 1, further comprising:
an auger disposed in the receptor chamber; and
a stir bar disposed in the receptor chamber and adapted to drive the auger,
wherein the auger driven by the stir bar causes at least a portion of the flow of fluid to recirculate through the conduit and the receptor chamber, whereby said at least a portion of the flow of fluid is transmitted from the receptor chamber through the conduit and back into the receptor chamber.

3. A diffusion cell as in claim 1, wherein the third port is above and in fluid communication with the second port of the conduit.

4. A diffusion cell as in claim 1, wherein at least a portion of the conduit is outside the receptor chamber.

5. A diffusion cell as in claim 1, wherein the conduit is adapted to transmit at least a portion of the flow of fluid from the upper end of the receptor chamber near the membrane through the second port into the conduit and downward to the first port and into the lower end of the receptor chamber.

6. A diffusion cell as in claim 1, wherein the conduit is substantially vertical.

7. A diffusion cell as in claim 6, wherein the conduit has a sampling port permitting removal of at least some of any contents of the receptor chamber.

8. A diffusion cell as in claim 7, wherein removal of at least some of any contents of the receptor chamber through the sampling port is performed manually with a pipette tip.

9. A diffusion cell as in claim 7, wherein removal of at least some of any contents of the receptor chamber through the sampling port is performed automatically with an automated pipette tip.

10. An automated system of diffusion cells, comprising:
a plurality of diffusion cells, each diffusion cell comprising
a donor chamber for containing a liquid and a media in the liquid, the donor chamber having a top and a bottom opposite the top;
a receptor chamber below the donor chamber and in fluid communication with the donor chamber, the receptor chamber having an upper end and a lower end opposite the upper end;
a membrane between and in contact with the bottom of the donor chamber and the upper end of the receptor chamber, the membrane adapted to diffuse a portion of the media in the liquid from the donor chamber to the receptor chamber;
a substantially vertical conduit having a first port near, and in fluid communication with, the lower end of the receptor chamber and a second port above the first port, the second port being near, and in fluid communication with, the upper end of the receptor chamber;
a bubble trap in fluid communication with the upper end of the receptor chamber and having a third port positioned higher than the second port of the conduit;
an auger disposed in the receptor chamber; and
a magnetically driven stir bar disposed in the receptor chamber and adapted to drive the auger,
wherein the auger driven by the magnetically driven stir bar causes a flow of fluid to recirculate through the substantially vertical conduit and the receptor chamber, whereby at least a portion of the flow of fluid is transmitted from the receptor chamber through the substantially vertical conduit and back into the receptor chamber, and wherein recirculation of at the least a portion of the flow of fluid through the substantially vertical conduit and the receptor chamber removes at least some bubbles from underneath the membrane in the receptor chamber and transports at least some of said bubbles from the receptor chamber to the bubble trap.

11. An automated system as in claim 10, wherein at least a portion of the substantially vertical conduit is outside the receptor chamber and the substantially vertical conduit is adapted to transmit the at least a portion of the flow of fluid from the upper end of the receptor chamber near the membrane through the second port into the substantially vertical conduit and downward to the first port and into the lower end of the receptor chamber.

12. An automated system as in claim 11, wherein the substantially vertical conduit has a sampling port permitting removal of at least some of any contents of the receptor chamber.

13. An automated system as in claim 12, wherein removal of at least some of any contents of the receptor chamber through the sampling port is performed automatically with an automated pipette tip.

14. An automated system as in claim 10, further comprising a magnetic console adapted to magnetically drive the magnetically driven stir bar.

15. A method for removing bubbles from a diffusion cell, comprising the steps of: providing a diffusion cell, comprising a donor chamber for containing a liquid and a media in the liquid, the donor chamber having a top and a bottom opposite the top;

a receptor chamber below the donor chamber and in fluid communication with the donor chamber, the receptor chamber having an upper end and a lower end opposite the upper end;

a membrane between and in contact with the bottom of the donor chamber and the upper end of the receptor chamber, the membrane adapted to diffuse a portion of the media in the liquid from the donor chamber to the receptor chamber;

a substantially vertical conduit having a first port near, and in fluid communication with, the lower end of the receptor chamber and a second port above the first port, the second port being near, and in fluid communication with, the upper end of the receptor chamber;

a bubble trap in fluid communication with the upper end of the receptor chamber and having a third port positioned higher than the second port of the conduit;

an auger disposed in the receptor chamber; and a magnetically driven stir bar disposed in the receptor chamber and adapted to drive the auger; and driving the auger by the magnetically driven stir bar, thereby causing at least a portion of a flow of fluid to recirculate through the substantially vertical conduit and the receptor chamber, whereby said at least a portion of the flow of fluid is transmitted from the receptor chamber through the substantially vertical conduit and back into the receptor chamber, wherein recirculation of at the least a portion of the flow of fluid through the substantially vertical conduit and the receptor chamber removes at least some bubbles from underneath the membrane in the receptor chamber and transports at least some of said bubbles from the receptor chamber to the bubble trap.

16. A method as in claim 15, wherein at least a portion of the substantially vertical conduit is outside the receptor chamber and the substantially vertical conduit is adapted to transmit the at least a portion of the flow of fluid from the upper end of the receptor chamber near the membrane through the second port into the substantially vertical conduit and downward to the first port and into the lower end of the receptor chamber.

17. A method as in claim 16, wherein the substantially vertical conduit has a sampling port permitting removal of at least some of any contents of the receptor chamber.

18. A method as in claim 17, wherein removal of at least some of any contents of the receptor chamber through the sampling port is performed automatically with an automated pipette tip.

19. A method as in claim 15, wherein a magnetic console magnetically drives the magnetically driven stir bar.

20. A diffusion cell, comprising:

a donor chamber for containing a liquid and a media in the liquid, the donor chamber having a top and a bottom opposite the top;

a receptor chamber below the donor chamber and in fluid communication with the donor chamber, the receptor chamber having an upper end and a lower end opposite the upper end;

a membrane between and in contact with the bottom of the donor chamber and the upper end of the receptor chamber, the membrane adapted to diffuse a portion of the media in the liquid from the donor chamber to the receptor chamber;

a substantially vertical conduit having a first port near, and in fluid communication with, the lower end of the receptor chamber and a second port above the first port, the second port being near, and in fluid communication with, the upper end of the receptor chamber;

a bubble trap in fluid communication with the upper end of the receptor chamber and having a third port positioned higher than the second port of the conduit;

an auger disposed in the receptor chamber, the auger having an upper end and a lower end; and a magnetically driven stir bar disposed in the lower end of the auger and adapted to drive the auger, wherein at least a portion of the substantially vertical conduit is outside the receptor chamber and the substantially vertical conduit is adapted to transmit a flow of fluid from the upper end of the receptor chamber near the membrane through the second port into the substantially vertical conduit and downward to the first port and into the lower end of the receptor chamber, wherein the auger driven by the magnetically driven stir bar causes at least a portion of the flow of fluid to recirculate downward through the substantially vertical conduit into the lower end of the receptor chamber and upward through the receptor chamber to the upper end of the receptor chamber, whereby the at least a portion of the flow of fluid is transmitted from the upper end of the receptor chamber through the second port downward to the first port and back into the receptor chamber at the lower end, and wherein recirculation of the at least a portion of the flow of fluid through the substantially vertical conduit and the receptor chamber removes at least some bubbles from underneath the membrane in the receptor chamber and transports at least some of said bubbles from the receptor chamber through the substantially vertical conduit to the bubble trap.

21. A diffusion cell as in claim 20, wherein the substantially vertical conduit has a sampling port permitting removal of at least some of any contents of the receptor chamber.

22. A diffusion cell as in claim 21, wherein removal of at least some of any contents of the receptor chamber through the sampling port is performed with a pipette tip.

* * * * *